United States Patent [19]

Moyzis et al.

[11] Patent Number: 5,064,948

[45] Date of Patent: Nov. 12, 1991

[54] CHROMOSOME SPECIFIC REPETITIVE DNA SEQUENCES

[75] Inventors: Robert K. Moyzis; Julianne Meyne, both of Los Alamos, N. Mex.

[73] Assignee: The United States of America as represented by the Department of Energy, Washington, D.C.

[21] Appl. No.: 155,451

[22] Filed: Feb. 12, 1988

[51] Int. Cl.$^5$ .................... C07H 21/04; C12Q 1/68
[52] U.S. Cl. ............................. 536/27; 435/6; 436/501; 436/510; 436/815; 935/19; 935/78
[58] Field of Search ............ 435/6; 436/501, 510, 436/815; 536/27; 935/19, 78

[56] References Cited

PUBLICATIONS

Fisher et al (1984), Proc. Natl. Acad. Sci (USA), vol. 81, pp. 520–524.
Huntington F. Willard, "Chromosome–Specific Organization of Human Alpha Satellite DNA," Am. J. Hum. Genet., 37, 524–532 (1985).
Y.–F. Lau, "Detection of Y–Specific Repeat Sequences in Normal and Variant Human Chromosomes Using In Situ Hybridization with Biotinylated Probes," Cytogenet. Cell Genet., 39, 184–187 (1985).
Laura Manuelidis, "Individual Interphase Chromosome Domains Revealed by In Situ Hybridization," Hum. Genet., 71, 288–293 (1985).
T. Cremer et al., "Detection of Chromosome Aberrations in the Human Interphase Nucleus by Visualization of Specific Target DNAs with Radioactive and Non–Radioactive In Situ Hybridization Techniques: Diagnosis of Trisomy 18 with Probe L1.84," Hum. Genet., 74, 346–352 (1986).
A. Lund Jorgensen et al., "Chromosome–Specific Subfamilies Within Human Alphoid Repetitive DNA," J. Mol. Biol., 187, 185–196 (1986).
P. Devilee et al., "Two Subsets of Human Alphoid Repetitive DNA Show Distinct Preferential Localization in the Pericentric Regions of Chromosomes 13, 18, and 21," Cytogenet. Cell Genet., 41, 193–201 (1986).
P. Devilee et al., "Sequence Heterogeneity Within the Human Alphoid Repetitive DNA Family," Nucleic Acids Research, 14, No. 5, 2059–2073 (1986).
John S. Waye et al., "Genomic Organization of Alpha Satellite DNA on Human Chromosome 7: Evidence for Two Distinct Alphoid Domains on a Single Chromosome," Molecular and Cellular Biology, 7, No. 1, 349–356 (Jan. 1987).
John S. Waye et al., "Chromosome–Specific Alpha Satellite DNA From Human Chromosome 1: Hierarchical Structure and Genomic Organization of a Polymorphic Domain Spanning Several Hundred Kilobase Pairs of Centrometric DNA," Genomics, 1, 43–51 (1987).
John S. Waye et al., "Organization and Evolution of Alpha Satellite DNA from Human Chromosome 11," Chromosoma, 95, 182–188 (1987).
R. K. Moyzis et al., "Human Chromosome–Specific Repetitive DNA Sequences: Novel Markers for Genetic Analysis," Chromosoma, 95, 375–386 (1987).
Kong H. Choo et al, "Genomic Organization of Human Centromeric Alpha Satellite DNA: Characterization of a Chromosome 17 Alpha Satellite Sequence," DNA, 6, No. 4, 297–305 (1987).

Primary Examiner—Robert A. Wax
Assistant Examiner—Ardin H. Marschel
Attorney, Agent, or Firm—Ray G. Wilson; Paul D. Gaetjens; William R. Moser

[57] ABSTRACT

A method is provided for determining specific nucleotide sequences useful in forming a probe which can identify specific chromosomes, preferably through in situ hybridization within the cell itself. In one embodiment, chromosome preferential nucleotide sequences are first determined from a library of recombinant DNA clones having families of repetitive sequences. Library clones are identified with a low homology with a sequence of repetitive DNA families to which the first clones respectively belong and variant sequences are then identified by selecting clones having a pattern of hybridization with genomic DNA dissimilar to the hybridization pattern shown by the respective families. In another embodiment, variant sequences are selected from a sequence of a known repetitive DNA family. The selected variant sequence is classified as chromosome specific, chromosome preferential, or chromosome nonspecific. Sequences which are classified as chromosome preferential are further sequenced and regions are identified having a low homology with other regions of the chromosome preferential sequence or with known sequences of other family members and consensus sequences of the repetitive DNA families for the chromosome preferential sequences. The selected low homology regions are then hybridized with chromosomes to determine those low homology regions hybridized with a specific chromosome under normal stringency conditions. In accordance with the invention, oligomers are provided which are useful in forming a probe for specific chromosome identification under normal stringency conditions.

3 Claims, No Drawings

CHROMOSOME SPECIFIC REPETITIVE DNA SEQUENCES

This invention is the result of a contract with the Department of Energy (Contract No. W-7405-ENG-36).

BACKGROUND OF INVENTION

This invention relates to chromosome identification and, more particularly, to identifying repetitive DNA sequences which hybridize to specific chromosomes.

As is well known, living cells include chromosomes, those structures which carry DNA genetic units. Specific sets of chromosomes determine the characteristics of the life associated with the DNA genetic units. Thus, human cells contain 24 different chromosome types (22 autosomes, X and Y) and the number and arrangement of chromosomes within the cell are indicative of various normal and abnormal developments. By way of example, normal cells contain a pair of each type autosome and the presence of three of a chromosome type (trisomy) may be indicative of an abnormal condition. Trisomy 9 (i.e., three number 9 chromosomes) is indicative of a syndrome which is fatal within a few days of birth. Trisomy 16 is present in one-third of all spontaneous abortions that contain chromosome trisomies. Trisomy 21 is indicative of Down's syndrome.

Repetitive DNA clones have been described which hybridize to groups of human chromosomes, often with a prominent site of hybridization on only one or two autosomes. See, e.g., A. R. Mitchell et al., "Molecular hybridization to meiotic chromosomes in man reveals sequence arrangement on the No. 9 chromosome and provides clues to the nature of 'parameres',"  Cytogenet. Cell Genet. 41: 89-95 (1986), which teaches a probe, Xbl, which hybridizes preferentially, but not exclusively, with chromosome 9.

It has been suggested that each human chromosome may be characterized by one or more distinct subsets of alpha satellite DNA. See, e.g., P. Devilee et al., "Two Subsets of Human Alphoid Repetitive DNA Show Distinct Preferential Localization in the Pericentric Regions of Chromosomes 13, 18, and 21," Cytogenet. Cell Genet. 41, 193-201 (1986); A. Lund Jorgensen et al., "Chromosome-Specific Subfamilies Within Human Alphoid Repetitive DNA," J. Mol. Biol. 187, 185-196 (1986). Indeed, the enrichment of one or a few distinct subfamilies on individual chromosomes is reported. However, no process is taught for systematically determining nucleotide sequences which form chromosome specific probes. Further, no probes are taught which are chromosome specific under a normal stringency requirement for a positive chromosome identification after in situ hybridization of the probe with chromosomes within a cell.

It will be appreciated that the chromosome specificity of chromosome preferential DNA probes identified in the prior art may be improved by increasing the stringency under which hybridization is attempted. However, hybridization under conditions of high stringency may not obtain reproducible results. While only specific chromosomes may be tagged, not every such chromosome may be tagged, a clearly unacceptable condition for a routine clinical application. Further, high stringency levels frequently reduce the size and/or intensity of the hybridization site, requiring increased amplification of the fluorescent signal or longer time of autoradiographic exposure. These conditions increase the nonspecific background errors from the measurements. Probes that are chromosome specific after hybridization at normal stringency and a single amplification step or short exposure would be more useful for most applications, especially for identification and quantitation of chromosomes in interphase nuclei.

The ability to tag specific human autosomal chromosomes in interphase nuclei would allow investigations of the three-dimensional structure of the nucleus to be conducted and provide an approach to chromosome analysis where the isolation of metaphase chromosomes is inconvenient, difficult, or impossible. However, any cross hybridization between a chromosome "specific" probe sequence and other chromosomes dilutes the usefulness of the probe, especially for hybridization to interphase nuclei. The present invention provides a process for identifying repetitive nucleotide sequences which hybridize in situ to specific chromosomes under normal stringency conditions to enable such investigations and analysis to be reliably conducted.

Accordingly, it is an object of the present invention to identify repetitive nucleotide sequences which are chromosome specific under conditions of normal stringency.

It is another object of the present invention to enable in situ identification of chromosomes in intact cellular nuclei.

Still another object of the present invention is to provide a method for determining probe sequences which contain only that portion of a repeat unit that is enriched on or unique to the chromosome being identified.

One other object of the present invention is to identify chromosome specific nucleotide sequences having a length that can be synthesized.

SUMMARY OF INVENTION

To achieve the foregoing and other objects, and in accordance with the purposes of the present invention, as embodied and broadly described herein, the process of this invention may comprise a method for determining a repetitive nucleotide sequence effective to identify a specific chromosome under normal conditions of stringency for hybridizaton. A first repetitive nucleotide sequence is selected from a variant sequence within a sequence of a known repetitive DNA family. The first repetitive nucleotide sequence is then hybridized to classify the sequence as chromosome specific, chromosome preferential, or chromosome nonspecific. The classified chromosome preferential sequences are then examined to determine regions which have a low homology with other regions of the chromosome preferential sequence, which low homology regions are effective to hybridize with a specific chromosome under the normal stringency conditions.

In another characterization of the present invention, a method is provided for selecting chromosome specific repetitive DNA sequences from a library of recombinant DNA clones having families of repetitive sequences. First clones are selected from the library with a low homology with the sequence of repetitive DNA families to which the first clones respectively belong. The selected first clones are hybridized to total genomic DNA and variant clones are selected which have a hybridization pattern which is dissimilar to a predominant hybridization pattern shown by the respective families. The variant clones are then hybridized with chromosomes and classified as chromosome specific, chromosome preferential, or chromosome nonspecific. The chromosome preferential clones are further sequenced to determine regions having a sequence with low homology relative to known sequences of other family members and consensus sequences of the repetitive DNA families for the chromosome preferential clones. Those low homology regions are further hybridized to determine chromosome specific sequences effective to provide in situ chromosome specificity at a normal stringency level.

In yet another characterization of the present invention, oligomers are provided having a nucleotide sequence determined in accordance with the above processes. The oligomers are effective to provide a probe which hybridizes with a specific chromosome.

DETAILED DESCRIPTION

In accordance with the present invention, chromosome specific nucleotide sequences are determined by identifying significant local sequence divergences of a repetitive DNA family. It has been found that certain regions of chromosome preferential repeat units are primarily responsible for chromosome specific hybridization. As herein described, such variant sequences can yield probes which are chromosome specific under stringency levels of 80% or less. An effective probe contains tandem arrays of the selected sequence to hybridize with a tandem array of the specific chromosome to provide a localized fluorescence for positive identification.

Repetitive DNA is that part of the total DNA of a species, the genome, represented by sequences that are present many times, often in tandem arrays. When genomic DNA is cut into relatively short fragments and the two strands of the double helix are separated (denatured), the sequences of repetitive DNA rejoin (reassociate) at a more rapid rate than sequences that are present only once or a few times within the genome because there are many more chances for them to find their complementary sequence. This characteristic allows the formation of libraries of DNA fragments that have a large number of repetitive sequences.

The human genome contains several families of repetitive DNA. Although present in many sites within the genome, mixtures of repetitive sequences form large blocks at the centromere of each chromosome. Repetitive sequences have the capacity for rapid evolution; indeed, even homologues can have different repetitive sequences as a result of substitution, insertion, or deletion of individual bases within the sequences. Thus, tandem repetitive sequences should be available to uniquely identify each chromosome and to specifically hybridize with a probe having a sufficiently homologous tandem array.

The families of repetitive DNA can be identified by the arrangement of DNA bases within the repeat unit. For example, alpha satellite DNA sequences are units with variable numbers of tandem sequences of about 170 base pairs long, and satellite 2 DNA sequences have repeat units about 26 base pairs long. Most repetitive DNA families have a predominant form. When the entire family is isolated, a large number of the sequences present are very much alike (homologous).

The rest of the sequences form subfamilies. These are groups of sequences that have the same arrangement as the predominant form but have undergone base substitutions, deletions, and/or insertions. These changes create sites within the related sequences at which complementary strands cannot base pair with other sequences within the family. The proportion of these changes determines the relationship between any two sequences, i.e. homologous (sameness) or divergent (difference).

Some subfamilies are identified as variants, with sufficient divergence from the predominant form that they no longer can reassociate, or hybridize with the predominant form, under normal stringency conditions of temperature, concentration, and time. The ability of related sequences to hybridize at a given homology can be controlled by the stringency conditions imposed upon reassociation. The higher the stringency conditions, the greater the homology which is required to match each sequence. Under normal conditions, at least 80% of the bases within a sequence must match for the two strands to reassociate. As used herein, a low homology is a homology less than that needed for normal reassociation, i.e., less than about 80%.

In accordance with this invention, repetitive nucleotide sequences are selected and compared with DNA sequences of the respective repetitive DNA families. The present process seeks DNA sequences which have a low homology and a corresponding low likelihood of hybridizing with their family members which are generally present in several chromosomes in the human genome. Such nucleotide sequences have a relatively high probability of hybridizing with only specific chromosomes, if they hybridize at all. The more variant the sequence, the more specific the chromosome hybridization. Thus, DNA probes containing one or more copies of the low homology sequence can be used to identify specific chromosomes by in situ hybridization with cellular chromosomes.

A library of human repetitive DNA sequences has been constructed using conventional techniques. Purified human placental DNA was physically sheared into fragments with an average length of 3000–4000 base pairs. The DNA was denatured and allowed to reassociate under conditions that promoted the reassociation of repetitive DNA sequences. The resulting fragments were digested by S1 nuclease and processed to obtain double stranded repetitive DNA. The resulting double stranded repetitive DNA was cloned into the PstI site of plasmid pBR322 by G:C tailing with terminal transferase. The resulting plasmids were then grown in a bacterial system to form a clone containing many plasmids, each containing the same repetitive DNA sequence. The library clones are identified as pHuR (plasmid Human Repeat) clones and assigned an identification number. All of the pHuR clones identified herein are available from the pHuR library of Los Alamos National Laboratory, Los Alamos, N. Mex.

In one embodiment of the present invention, recombinant DNA clones are selected from the library and chromosome specific sequences are identified by the following procedure:

1. The repetitive DNA inserts are removed from the plasmid by PstI digestion and recloned in the M13 vector. In a first selection, the clones are partially sequenced using known techniques to determine the repetitive DNA family represented by a clone. Those clones containing sequences with a low homology (i.e., less than about 80% homology) with the sequence of the predominant family member are selected for further study.

2. The first selected clones are then hybridized to total genomic DNA on Southern blot gels. The pattern of hybridization is compared to that of the predominant sequence of the respective family. Those clones that do not show the same pattern as the predominant sequence are considered variants and are selected for chromosomal specificity testing.

3. The variant clones are hybridized to chromosomes under no more than normal stringency conditions and then classified as chromosome specific (hybridizes only to one chromosome), chromosome preferential (hybridizes mostly to one chromosome, but some to others), or chromosome nonspecific.

a. In one characterization method, a slot blot hybridization technique is used. Individual human chromosomes are sorted by flow cytometry and placed in separate slots on a filter. Radioactive DNA from the variant clone (probe) is hybridized to the filter blot, but will only reassociate to those chromosomes containing DNA sequences with 70-80% homology with the probe. The excess probe material is washed away and the remaining radioactivity can be detected on the slots of those chromosomes containing sequences sufficiently homologous to hybridize with the probe.

b. In another method, the repetitive DNA clone is hybridized in situ to chromosomes. The repetitive DNA clone is labeled with biotin and hybridized to human metaphase chromosomes. The probe will reassociate only at those sites on the chromosome with complementary sequences, usually at or near the centromere. The biotinylated probe that hybridized with the chromosomes is detected by avidin molecules with a fluorescent dye bound to them. The sites of hybridization can be observed through a fluorescent microscope.

4. The chromosome preferential clones are subjected to further analysis to determine whether there are sequences included within a variant clone which exhibit chromosomal specificity. The analysis technique depends on the availability of restriction sites within the clone for use in cutting natural fragments.

a. If restriction sites are available, the sequences of regions between restriction sites are determined and compared to the known sequences of other family members and to the consensus sequence of the repetitive DNA family. A consensus sequence is determined by comparing all the bases in each position of the repeat unit for all the known members of the family or subfamily and recording the base most frequently present at each base position. Those restriction fragments with less than 75% homology to the known family and consensus sequences are cut from the clone, reinserted in plasmids, and hybridized to metaphase chromosomes to further evaluate specificity.

b. If insufficient restriction sites are available, the entire clone sequence must be compared to known family and consensus sequences. A short region, e.g., 20–50 nucleotides, with the least homology is then selected and the sequence is synthesized using a DNA synthesizer to generate the specified sequence. The synthetic DNA is tailed with a biotinylated base and hybridized to metaphase chromosomes to evaluate chromosomal specificity. Using a conventional synthesizer, variations of known sequences, or portions of known sequences for which no natural DNA is available, can simply be synthesized and tested for chromosomal specificity.

Two repetitive DNA clones which are chromosome specific have been identified directly from the library. pHuR 98 hybridized specifically to chromosome position 9 qh. The pHuR 98 repeat sequence consists of the 10 nucleotide sequence CCAACCCGAGT, followed by diverged 5 nucleotide GGAAT repeats. The complete repeat spacings present in this clone are 54 and 45 nucleotides in length, separated by a truncated repeat of 29 nucleotides. The entire sequence of pHuR 98 is set out in Table A.

A second recombinant DNA clone, pHuR 195, showed specific hybridization to chromosome position 16 qh after in situ hybridization to normal human metaphase chromosomes. pHuR 195 is a variant of human DNA satellite 2 and has a "core" sequence of a conserved six nucleotide CATCAT followed by four divergent GGAAT sequences. The core sequences are spaced by various lengths of more highly diverged DNA sequences, varying from 0 to 49 nucleotides. The entire sequence of pHuR 195 is set out in Table B.

The ability of pHuR 98 and pHuR 195 to hybridize to specific chromosomes indicated that chromosomes contain tandem arrays of variant sequences which could uniquely identify the specific chromosome. Another chromosome specific repetitive DNA sequence was then identified and synthesized using a process according to the present invention. Alpha satellite DNA clones were selected for use as the starting material, with alphoid clones isolated from the plasmid human repeat library. A first clone, pHuR 22, was then selected because it did not cross hybridize with the predominant dimer-tetramer form of alphoid DNA. When hybridized at 70% homology cutoff to a slot blot of human chromosomes sorted by flow cytometry, 30–35% of the radiolabeled probe was bound to the chromosome 17 slot. About 2–5% of the probe also bound to each of several other chromosomes, but the clone sequence was identified as showing a chromosome preferential behavior.

Biotinylated pHuR 22 was then hybridized to metaphase chromosomes.

TABLE A

| pHuR98.Seq Length: 158 |
| --- |
| 1<br>5'aatcaacccg agtgcaatcg aatggaatcg aatgaatgga atgcaatgga<br>51<br>atggattcaa cttgaatgga atggaaagaa tggaatcaac acgagtggaa<br>101<br>tggcatggat tggaatggaa tggaatggaa tcaacccgag tacaggaatg<br>151<br>gaatggaa3' |

TABLE B

| pHuR195.Seq Length: 545 |
| --- |
| 1<br>5'atcatcaaat ggaatcgaat ggaatcatct aatgaacttg aaaggaatca<br>51<br>tcatcaaatg aagtcaaatg gaataaccaa atcgacatga atggaatcat<br>101<br>cattgaatag aatcgaatgg attcattaaa tgggctagaa tggaatcatc<br>151<br>tgtgaacgga ttcaaaggga atcatcatcg aatggaatcg aatggaaatg<br>201<br>tcaaccaatt gaatcatcat ggaattgaat cgaatggctc actgtcgaat<br>251<br>caaatcaaat ggaatcaatc aatccgtaat ggaattgaat ggaaacaatg |

TABLE B-continued pHuR195.Seq  Length: 545

```
301
aaaggaattg  aatggaatca  tcattgaatg  gaacccgaat  gaaatcatca
351
acgaatggaa  tccaatgtaa  tcatcanngg  taagcactta  aggaatcatt
401
atccgaatgg  aattaaatga  aatctataat  ccgaatggaa  tccgaatgga
451
atcatcatcg  aatggaatgg  aatggaaacg  ttattgaatg  gaattaaatg
501
aaattaccga  aatgaatgaa  atggattgat  cattaaaggg  aatta3'
```

TABLE C pHuR22-1.Seq  Length: 214

```
1
5'ctgcagaatc  tgcaagtgca  tatttggacc  tctgtgagga  attcgttgga
51
aacgggataa  tttcagctga  ctaaacagaa  gcagtctcag  aatcttcttt
101
gtgatgtttg  cattcaaatc  cccgagttga  actttccttt  caaagttcac
151
atttgaaaca  ctcttttgc   aggatctaca  agtggatatt  tggacactct
201
gtgtcctcct  gcag3'
```

Under normal stringency conditions (50% formamide at 37° C.) there was preferential location of the probe to the centromeric region of chromosome 17, but minor sites of cross hybridization could be detected at the centromeres of chromosomes 1, 9, 20, and X in many of the metaphases. These minor sites were also detected in the interphase nuclei. Slight changes in probe concentration or stringency conditions increased the amount of cross hybridization; e.g. pHuR 22 hybridized to essentially all the centromeres after hybridization under low stringency conditions (30% formamide at 37° C.).

The predominant form of alphoid DNA on chromosome 17 is a 2.7 kb higher order repeat unit consisting of 16 monomers of approximately 170 bp each. When clone pHuR 22 was removed from the plasmid vector by PstI digestion prior to sequencing, two internal PstI sites produced fragments of 2.7, 1.5, and 0.2 kb lengths. The 2.7 kb insert was an entire higher order repeat. The 1.5 kb fragment was the last half of the repeat unit, and the 0.2 kb fragment was predominantly monomer 1, i.e. pHuR 22-1.

In situ hybridization of probes constructed from these fragments showed that the 2.7 kb fragment hybridized like pHuR 22, the 1.5 kb fragment was not specific, while the 0.2 kb fragment, pHuR 22-1, hybridized specifically to chromosome 17 under moderate stringency conditions (40% formamide at 37° C.). The individual monomers of the selected alphoid DNA share only 65-94% homology. Monomer 1 is one of the more divergent of these monomers. It also shows low homology when compared to monomers of other known alphoid DNAs and is less than 65% homologous to the consensus alphoid sequence. Thus, the specific hybridization of monomer 1 to chromosome 17 confirmed the preliminary selection process.

It was then determined that at least one region of the monomer 1 sequence was sufficiently unique that it might not cross hybridize with other alphas. The region from bp 141-151 of pHuR 22-1 contains a cluster of bases that differ from both human alpha I and II consensus sequences. A 42 bp oligomer containing this region was synthesized, spanning nucleotides 111-152 of pHuR 22-1. The oligonucleotide was biotinylated by terminal transferase tailing with bio-dCTP and hybridized to human metaphase chromosomes with 30% formamide at 37° C., a normal stringency level. The probe bound specifically to chromosome 17. The entire sequence of pHuR 22-1 with the chromosome 17 specific probe (underlined) is set out in Table C.

The synthesis of chromosome specific oligomers is not limited to sequences of diverged regions of native DNA probes. A nucleotide sequence can be selected from published consensus sequences of repeat families. An oligomer is synthesized with a repeat sequence from a highly divergent region of the published sequence. The chromosomal preference of the synthesized oligomer is then determined, as discussed above. Chromosomal specificity may be further enhanced by determining regions within the selected sequence having a low homology with other regions of the selected sequence.

Chromosome specific repetitive DNA markers provide a powerful tool for identifying human chromosomes, but the specificity of repetitive DNA probes is dependent upon the degree of homology of the probe sequence with the complex sequences of the various DNA subfamilies present in human chromosomes. Enrichment of a particular subfamily on an individual chromosome may not, by itself, impart chromosomal specificity. The presence of the same or closely related subfamilies on other chromosomes may lead to cross hybridization under normal stringency conditions and dilute the usefulness of the probe, especially for hybridization to interphase nuclei. Probes which are identified according to the present invention contain only that portion of the tandem repeat that is unique to the chromosome being identified. Sequence analysis can be used to determine which segments of the repeat sequence are most divergent and the probe can be shortened by restriction or synthesis to hybridize more specifically to the target chromosome using normal stringency conditions.

The above examples illustrate that chromosome specific probes can be formulated using the above identification process. While chromosome specific sequences have not been identified for each chromosome, the above process will inherently enable the identifications to be made. Thus, the present invention includes the oligomers identified by the above processes from which chromosome specific probes can be synthesized.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A DNA sequence for specific in situ hybridization to chromosome position 9 qh, consisting essentially of the DNA sequence of Table A.

2. A DNA sequence for specific in situ hybridization to chromosome position 16 qh, consisting essentially of the DNA sequence of Table B.

3. A DNA sequence for specific in situ hybridization to chromosome 17 consisting essentially of the sequence 5' cattcaaatc cccgagttga actttccttt caaagttac at 3'.

* * * * *